(12) United States Patent
Bankoski et al.

(10) Patent No.: US 9,050,147 B2
(45) Date of Patent: Jun. 9, 2015

(54) SYSTEM AND METHODS FOR MINIMALLY INVASIVE SPINE SURGERY

(75) Inventors: Brian Bankoski, West Grove, PA (US);
Robert Masson, Windermere, FL (US);
Mark Rossney, West Chester, PA (US);
Brian Schmidt, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 789 days.

(21) Appl. No.: 13/006,766

(22) Filed: Jan. 14, 2011

(65) Prior Publication Data

US 2011/0172674 A1    Jul. 14, 2011

Related U.S. Application Data

(60) Provisional application No. 61/335,961, filed on Jan. 14, 2010.

(51) Int. Cl.
| *A61B 17/58* | (2006.01) |
| *A61B 17/70* | (2006.01) |
| *A61B 17/17* | (2006.01) |
| *A61B 17/86* | (2006.01) |

(Continued)

(52) U.S. Cl.
CPC .......... *A61B 17/7079* (2013.01); *A61B 17/1735* (2013.01); *A61B 17/1757* (2013.01); *A61B 17/7011* (2013.01); *A61B 17/7037* (2013.01); *A61B 17/7091* (2013.01); *A61B 17/864* (2013.01); *A61B 19/54* (2013.01); *A61B 2017/0046* (2013.01); *A61B 2019/307* (2013.01)

(58) Field of Classification Search
USPC ................................................. 606/104, 105
See application file for complete search history.

(56) References Cited

U.S. PATENT DOCUMENTS

| 5,361,766 A | 11/1994 | Nichols |
| 7,250,052 B2 | 7/2007 | Landry et al. |

(Continued)

FOREIGN PATENT DOCUMENTS

| WO | WO 2004/041100 | 5/2004 |
| WO | WO 2007/011755 | 1/2007 |

(Continued)

OTHER PUBLICATIONS

Pennig, et al., "A Target Device for Placement of Implants in the Thoracolumbar Pedicles," The Journal of Bone and Joint Surgery, Sep. 1990, vol. 72-B, No. 5, p. 886-888.

*Primary Examiner* — Nicholas Woodall
(74) *Attorney, Agent, or Firm* — Baker & Hostetler LLP

(57) ABSTRACT

Methods and instruments are provided to allow access to a surgical site through a small incision while optimizing visualization of the patient anatomy. The instrumentation provide for the retraction of soft tissue, creation of a working envelope below the skin, and access to intervertebral discs and/or the surrounding bony structures for the purpose of performing various operative procedures including discectomy, laminectomy, and other spinal fixations. One set of disclosed instrumentation provides for the targeting of placement and trajectory of spinal fixation devices while reducing the number of instruments necessary needed to pass through the surgical incision. Another instrument disclosed herein allows for the compression of the intervertebral space through a very small incision. The instrument profile is minimized by using the same instrument that is used for tightening of the pedicle screws as one of the active components of the compression instrument.

17 Claims, 11 Drawing Sheets

(51) Int. Cl.
 *A61B 19/00* (2006.01)
 *A61B 17/00* (2006.01)

(56) References Cited

U.S. PATENT DOCUMENTS

| | | | |
|---|---|---|---|
| 7,465,306 B2 | 12/2008 | Pond et al. | |
| 7,491,218 B2 | 2/2009 | Landry et al. | |
| 7,563,264 B2 | 7/2009 | Landry et al. | |
| 7,686,814 B2 * | 3/2010 | Lim et al. | 606/105 |
| 7,691,132 B2 | 4/2010 | Landry et al. | |
| 7,914,558 B2 | 3/2011 | Landry et al. | |
| 8,034,084 B2 | 10/2011 | Landry et al. | |
| 8,075,565 B2 * | 12/2011 | Wilcox et al. | 606/86 A |
| 8,075,592 B2 | 12/2011 | Landry et al. | |
| 8,083,750 B2 | 12/2011 | Lim et al. | |
| 8,287,546 B2 * | 10/2012 | King et al. | 606/86 A |
| 8,491,588 B2 * | 7/2013 | Wall et al. | 606/86 A |
| 8,496,685 B2 | 7/2013 | Landry et al. | |
| 8,523,876 B2 | 9/2013 | Lim et al. | |
| 2005/0159757 A1 * | 7/2005 | Shluzas et al. | 606/105 |
| 2006/0009777 A1 * | 1/2006 | Lim et al. | 606/90 |
| 2006/0036255 A1 | 2/2006 | Pond et al. | |
| 2007/0005072 A1 | 1/2007 | Castillo et al. | |
| 2007/0016219 A1 | 1/2007 | Levine | |
| 2008/0177335 A1 | 7/2008 | Melkent | |
| 2010/0198272 A1 | 8/2010 | Keyer et al. | |

FOREIGN PATENT DOCUMENTS

| | | |
|---|---|---|
| WO | WO 2008/038284 | 4/2008 |
| WO | WO 2011/087826 | 7/2011 |
| WO | WO 2011/088284 | 7/2011 |

* cited by examiner

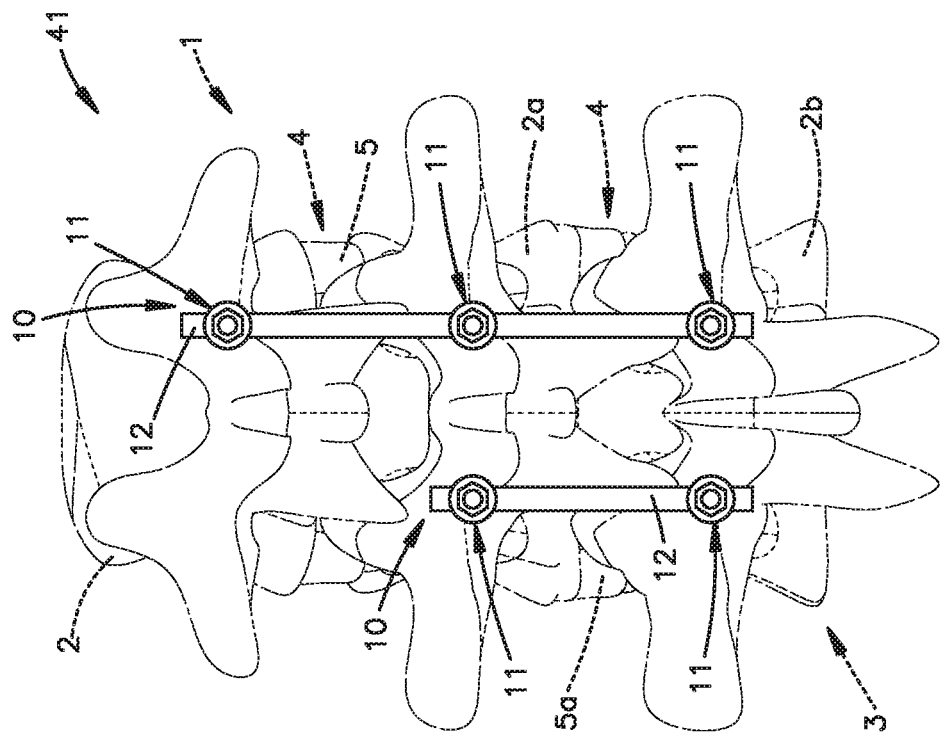
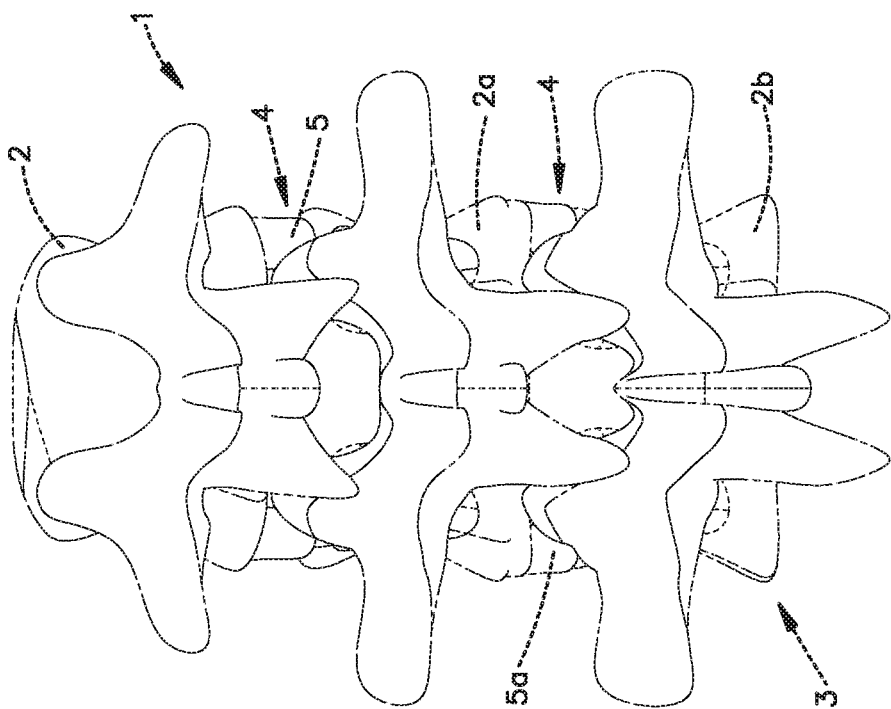

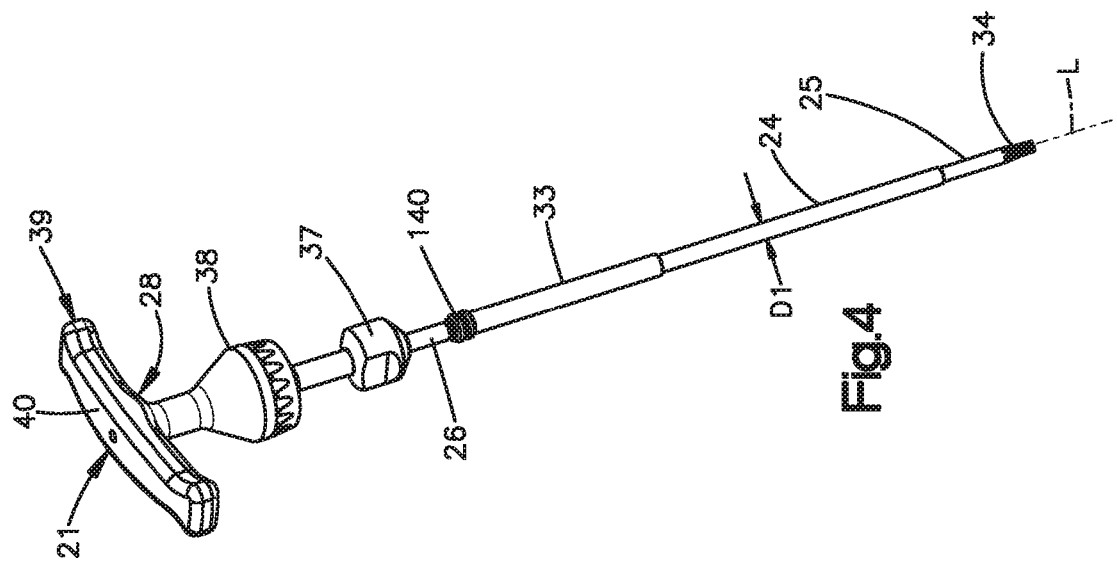
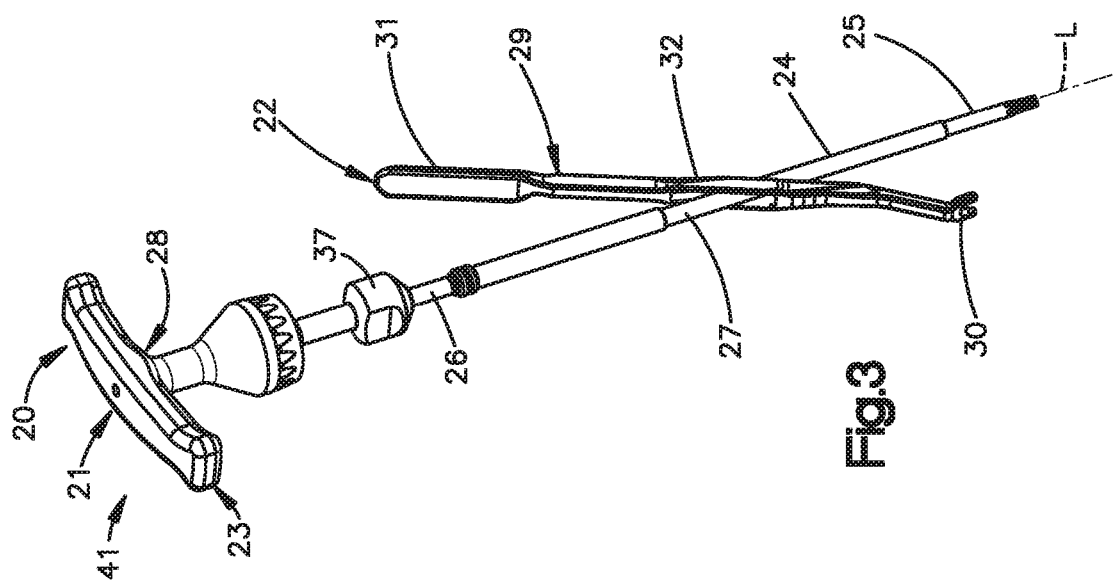

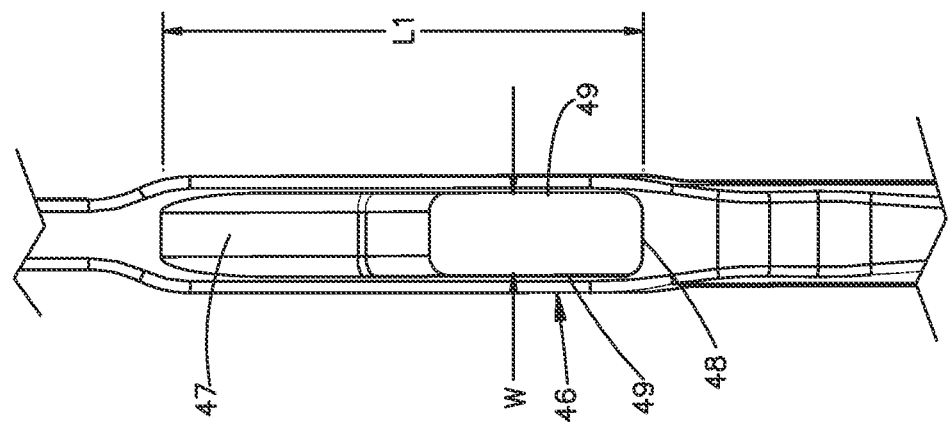
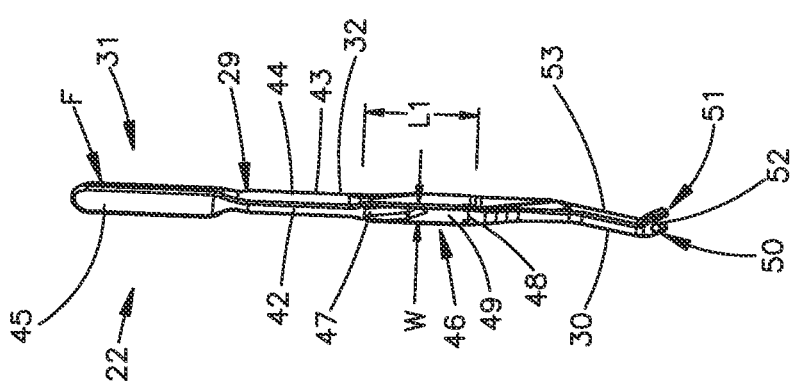

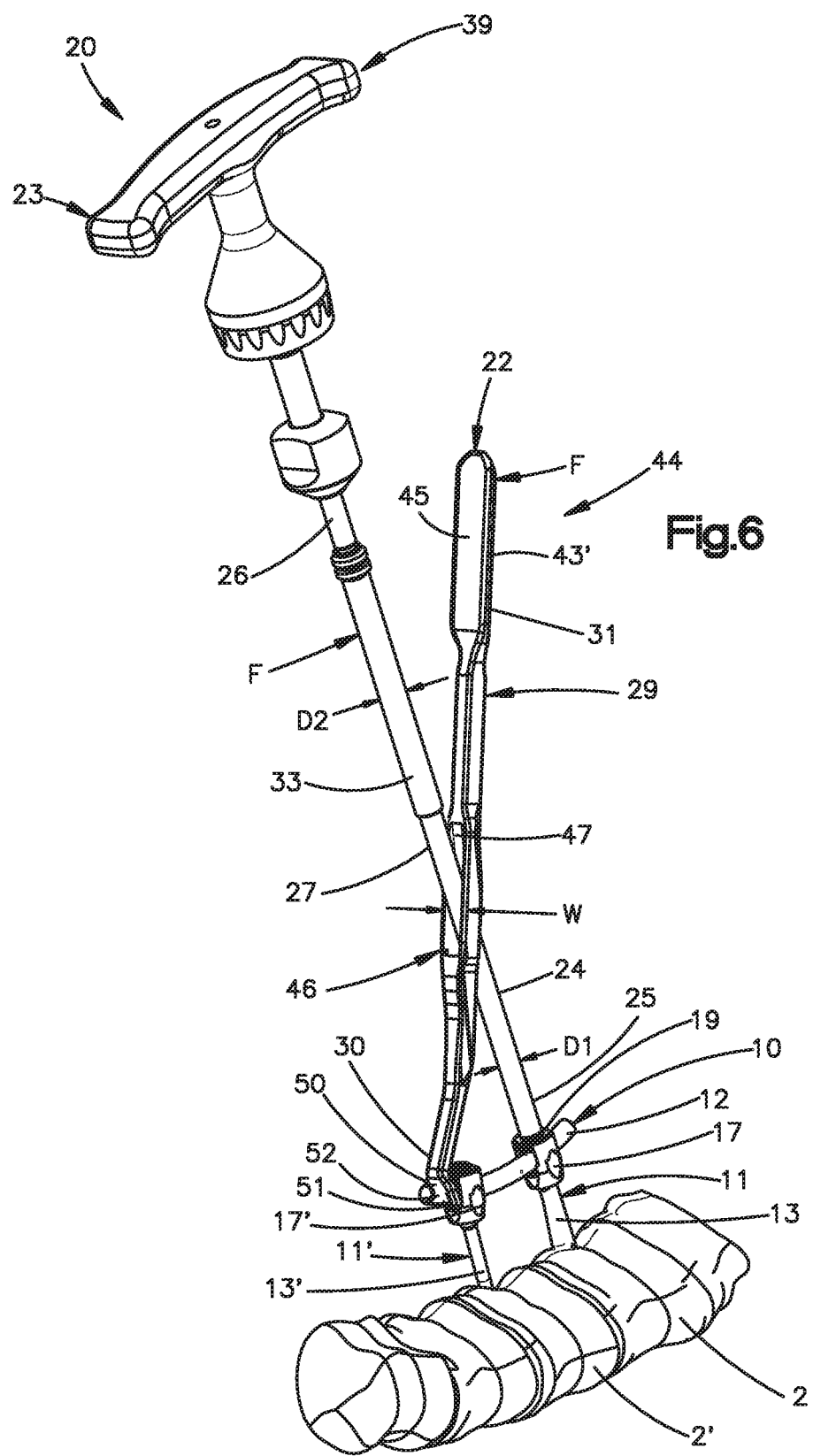

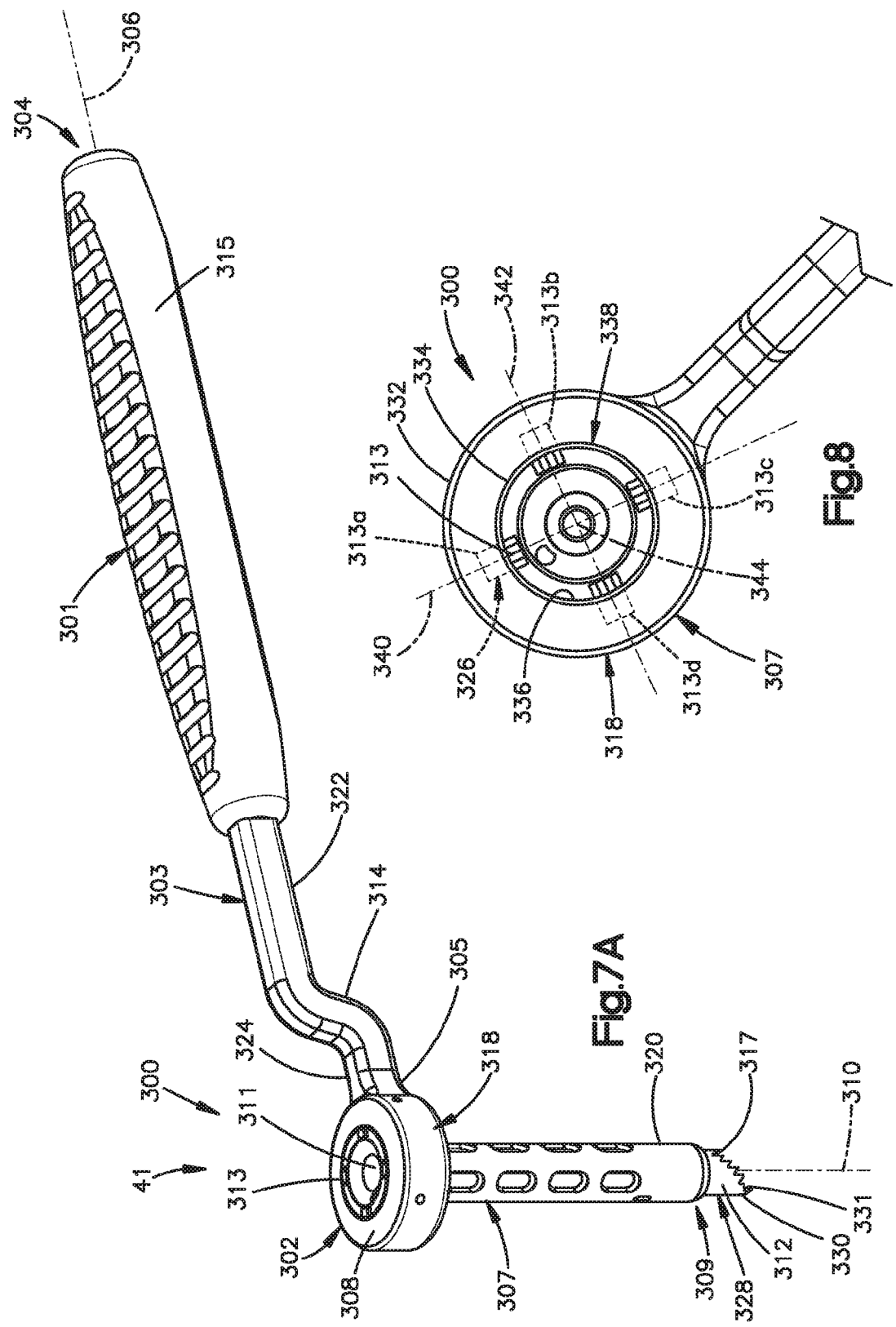

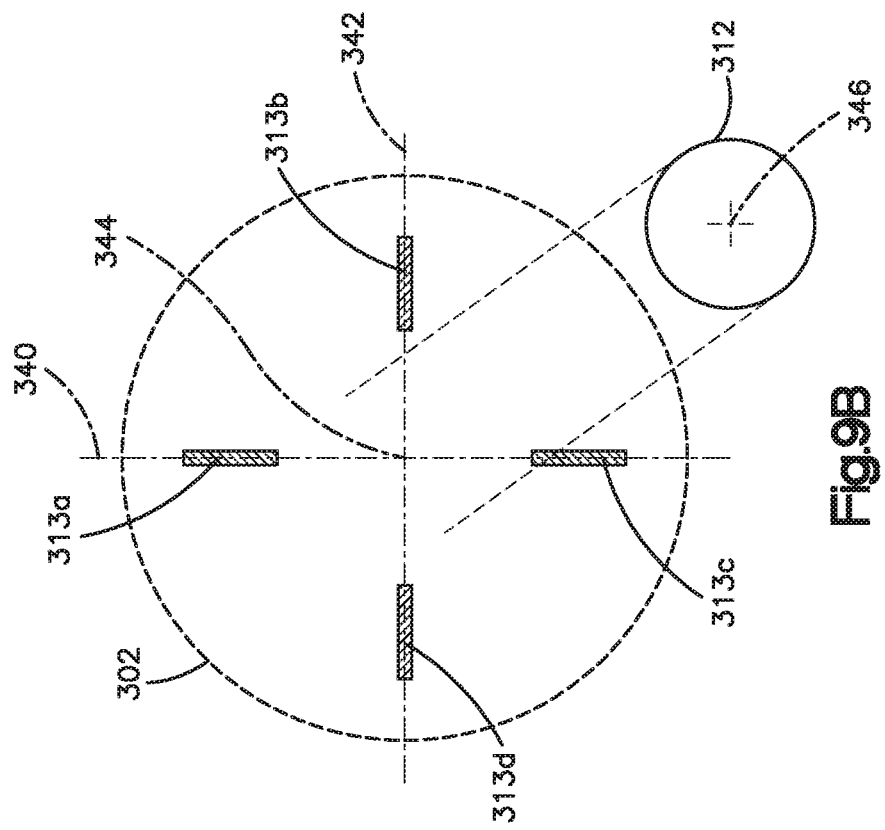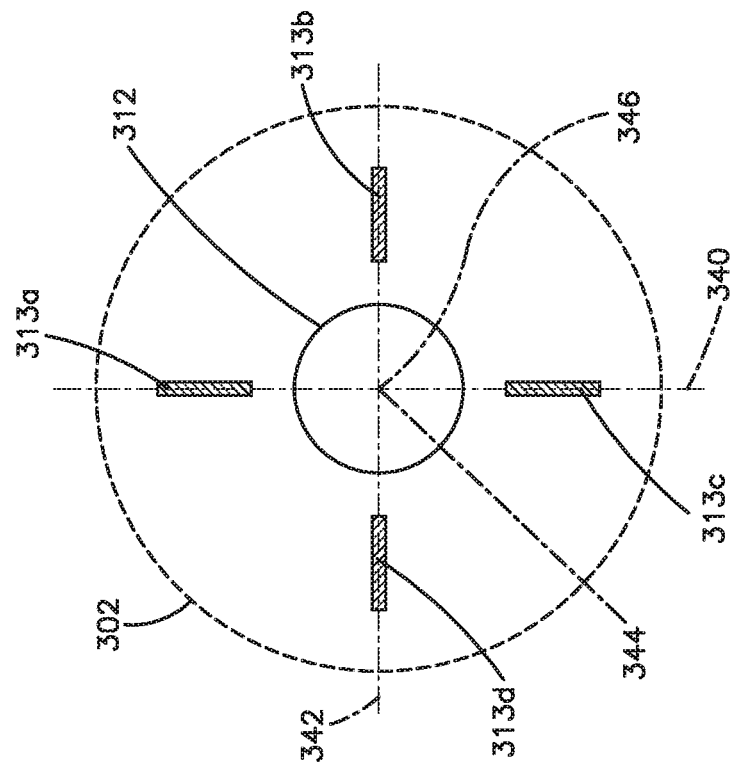

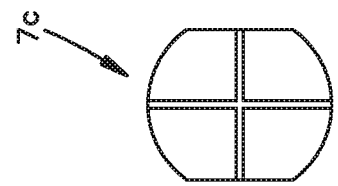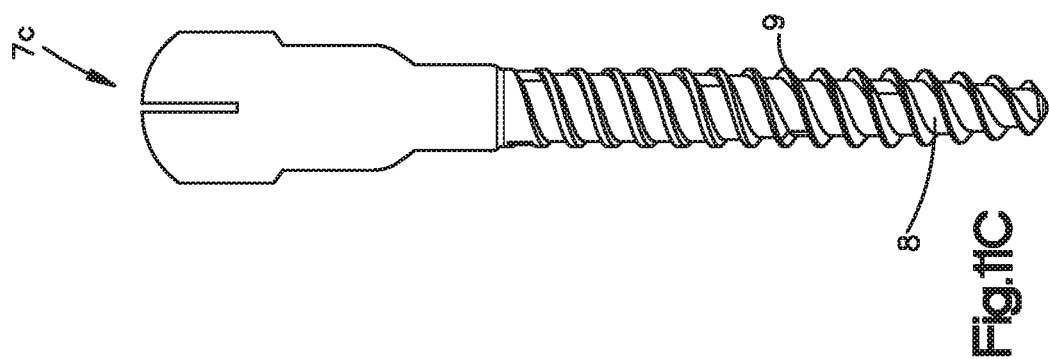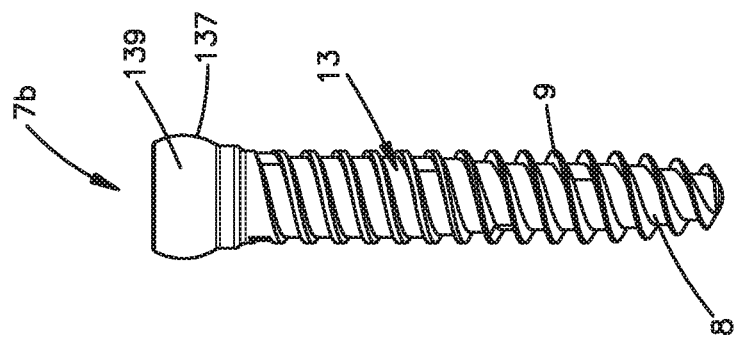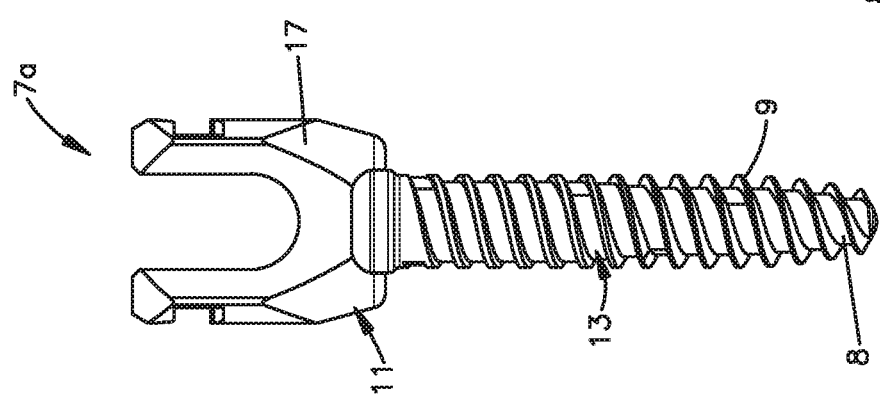

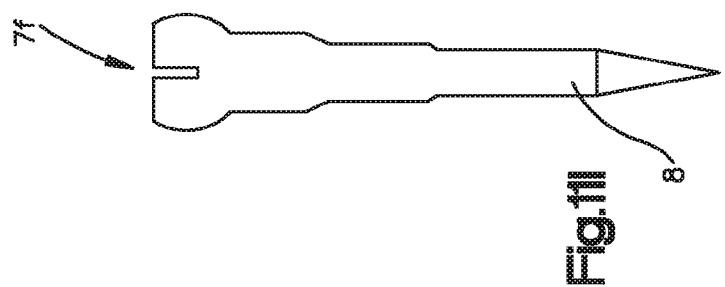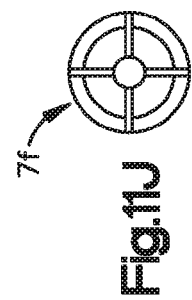
Fig.11I  Fig.11J
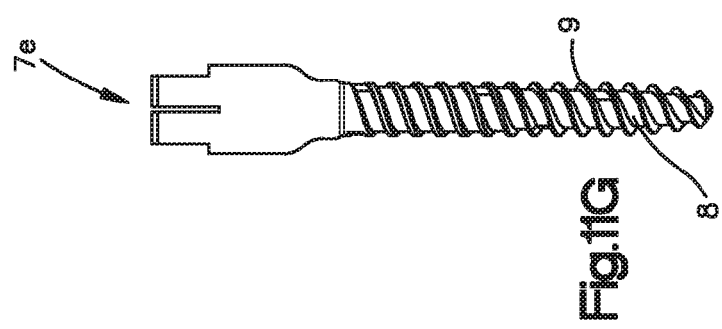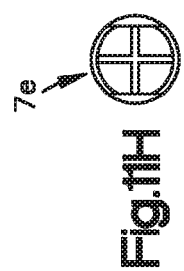
Fig.11G  Fig.11H
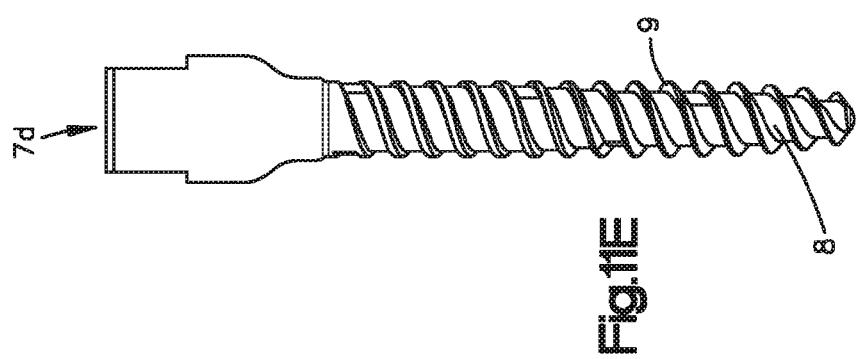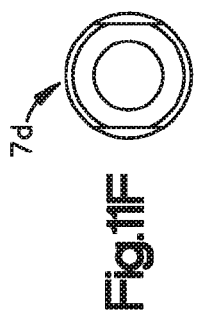
Fig.11E  Fig.11F

SYSTEM AND METHODS FOR MINIMALLY INVASIVE SPINE SURGERY

CROSS REFERENCE TO RELATED APPLICATIONS

This application claims benefit to U.S. Provisional Application Ser. No. 61/335,961, filed Jan. 14, 2010, the disclosure of which is hereby incorporated by reference as if set forth in its entirety herein.

BACKGROUND

Spinal fusion is a procedure that involves joining two or more adjacent vertebrae with a bone fixation device to restrict movement of the vertebra with respect to one another. Spinal fixation devices are used in spine surgery to align, stabilize and/or fix a desired relationship between adjacent vertebral bodies. Such devices typically include a spinal fixation rod, such as, for example, a relatively rigid fixation rod or a dynamic or flexible spinal fixation rod, etc. (collectively referred to herein as a spinal fixation rod), that is coupled to adjacent vertebrae by attaching the spinal fixation rod to various spinal fixation elements, such as, for example, hooks, bolts, wires, screws, such as pedicle screws, and the like. Surgeons may commonly choose to install multiple spinal fixation elements, as well as multiple spinal fixation rods, to treat a given spinal disorder.

Conventional surgical techniques for spinal fusion have involved the use of multiple instruments that sometimes require the use of more than one hand to operate. Thus, multiple surgeons often manipulate the instruments used during a spinal fusion surgery. Furthermore, conventional surgical techniques included long incisions that are associated with long and painful recovery times. Recently, minimally invasive surgical procedures for performing spinal fusion have been developed that generally provide access to and perform corrective surgery at a surgical site while imparting reduced trauma to the patient anatomy.

SUMMARY

In accordance with one embodiment, a surgical instrument includes a driver and an actuator. The driver is configured to apply a torque to a locking cap of a spinal fixation device, so as to lock the locking cap against a spinal fixation rod. The driver defines a proximal end and a distal end opposite the proximal end. The actuator defines a distal end that is configured to fit over the spinal fixation rod, and a proximal end opposite the distal end. The actuator includes a body that defines a recess sized to receive the driver such that the driver extends through the actuator and is rotatable with respect to the actuator.

BRIEF DESCRIPTION OF THE DRAWINGS

The foregoing summary, as well as the following detailed description of the preferred embodiments of the application, will be better understood when read in conjunction with the appended drawings. For the purposes of illustrating the surgical instruments and methods of the present application, there is shown in the drawings preferred embodiments. It should be understood, however, that the application is not limited to the specific embodiments and methods disclosed, and reference is made to the claims for that purpose. In the drawings:

FIG. 1A is a rear elevation view of a portion of a spinal region of a human spine, illustrating three adjacent vertebrae separated by respective intervertebral spaces;

FIG. 1B is a rear elevation view of the portion of the spinal region illustrated in FIG. 1A, whereby a pair of spinal fixation assemblies attached to the vertebrae after a spinal fusion surgery has been performed, the spinal fixation assembly including spinal fixation rods and spinal fixation devices;

FIG. 3 is a perspective view of a bone anchor manipulation instrument constructed in accordance with one embodiment including a torque assembly and an actuator;

FIG. 4 is a perspective view of the torque assembly illustrated in FIG. 3;

FIG. 5A is a perspective view of the actuator illustrated in FIG. 3, including a distal body portion, a proximal body portion and an intermediate body portion;

FIG. 5B is a top plan view of the intermediate body portion of the actuator illustrated in FIG. 5A;

FIG. 6 is a perspective view of the bone anchor manipulation instrument illustrated in FIG. 3, shown operably coupled to a pair of spinal fixation devices;

FIG. 7A is a perspective view of an anchor delivery instrument constructed in accordance with one embodiment including a handle and a guide;

FIG. 8 is a top plan view of the guide illustrated in FIG. 7A;

FIG. 9A is a schematic radio image of the guide illustrated in FIG. 8, shown in a desired orientation;

FIG. 9B is a schematic radio image of the guide illustrated in FIG. 8, shown in an undesired orientation;

FIG. 11A is a side elevation view of a fiducial marker illustrated as a spinal fixation device of the type illustrated in FIG. 2;

FIG. 11B is a side elevation view of a fiducial marker illustrated as a bone anchor of the spinal fixation device of the type illustrated in FIG. 11A;

FIG. 11C is a side elevation view of a fiducial marker constructed in accordance with another embodiment;

FIG. 11D is a top plan view of the fiducial marker illustrated in FIG. 11C;

FIG. 11E is a side elevation view of a fiducial marker constructed in accordance with another embodiment;

FIG. 11F is a top plan view of the fiducial marker illustrated in FIG. 11E;

FIG. 11G is a side elevation view of a fiducial marker constructed in accordance with another embodiment;

FIG. 11H is a top plan view of the fiducial marker illustrated in FIG. 11G;

FIG. 11I is a side elevation view of a fiducial marker constructed in accordance with another embodiment; and FIG. 11J is a top plan view of the fiducial marker illustrated in FIG. 11I.

DETAILED DESCRIPTION

Figure 2:
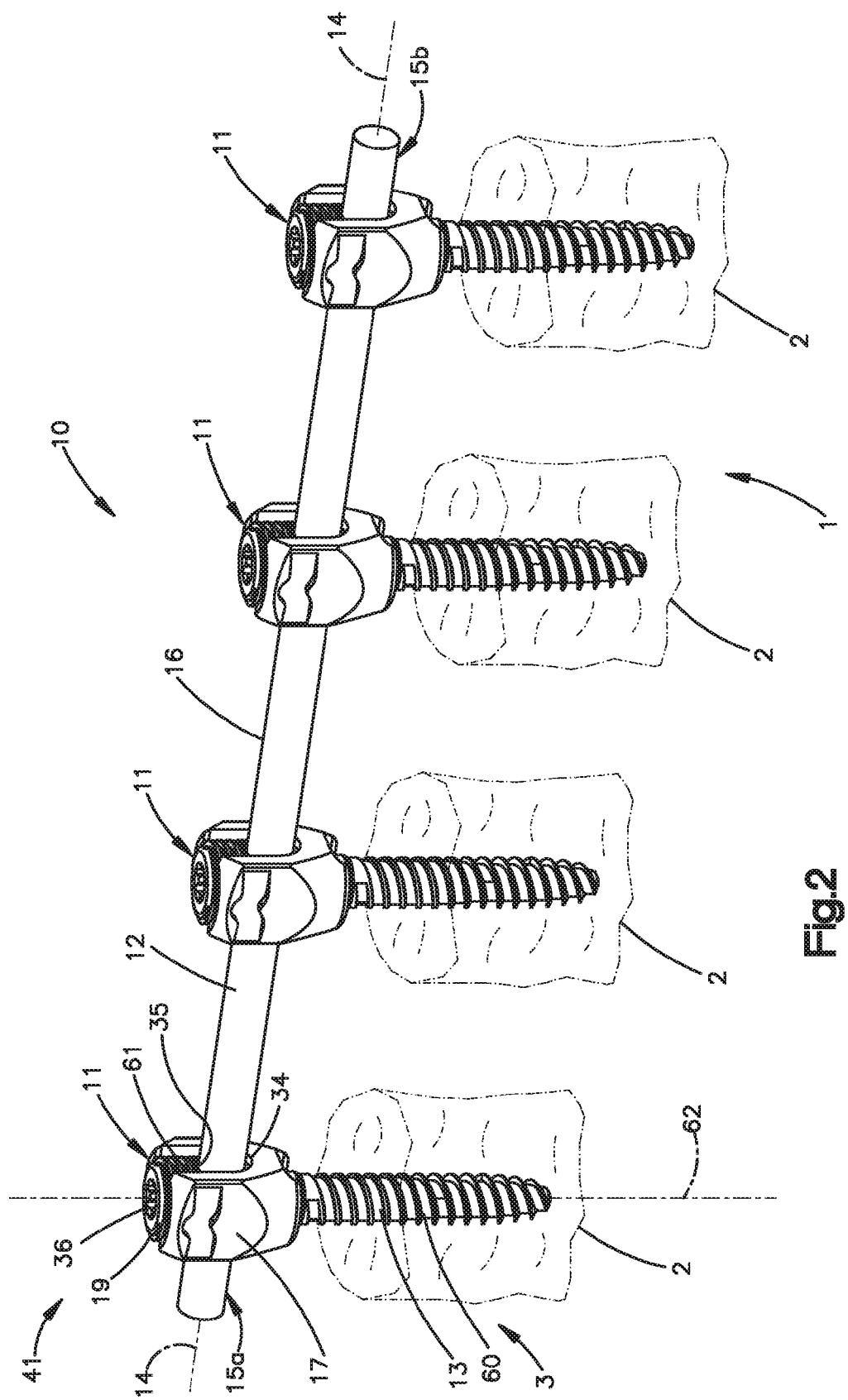
FIG. 2 is a perspective view of a spinal fixation device of the type illustrated in FIG. 1B.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical instrument. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Referring to FIG. 1A, a spinal region 1 of the human spine includes a plurality of adjacent vertebrae 2 arranged along a vertical spinal column 3. Adjacent vertebrae 2 are separated by respective intervertebral disc spaces 4 that can retain a vertebral disc 5. As illustrated, the spinal region 1 includes a superior vertebra 2a disposed above an inferior vertebra 2b and separated from the inferior vertebra 2b by a respective intervertebral disc space 5a. It should be appreciated that a discectomy can be performed on one or more intervertebral disc spaces 4 as desired that remove the vertebral disc 5 so as to reveal an intervertebral disc space 5a whereby the vertebral disc 5 has been removed. An artificial disc can be implanted in the intervertebral disc space 5a. Alternatively or additionally, the adjacent vertebrae 2 that define the intervertebral disc space can be fused.

For instance, referring to FIG. 1B, a surgical assembly 41 includes a spinal fixation assembly 10 that is configured to fuse or otherwise attach adjacent vertebrae 2 together. The spinal fixation assembly 10, and components thereof, can be constructed generally as described in U.S. patent application Ser. No. 12/669,224, filed Jul. 21, 2008, published as U.S. Publication No. 2010/0198272, the disclosure of which is hereby incorporated by reference as if set forth in its entirety herein. In accordance with the illustrated embodiment, the spinal fixation assembly 10 can includes a plurality of spinal fixation devices 11, for instance at least a pair of spinal fixation devices 11, and a spinal fixation rod 12 configured to be coupled to the spinal fixation devices 11. Accordingly, the spinal fixation rod 12 spans across at least one intervertebral disc space 4. The spinal fixation devices 11 are implanted into respective vertebrae 2, for instance into the pedicles of the vertebrae 2. The spinal fixation rod 12 extends through the spinal fixation devices 11 so as to operatively couple the respective vertebrae 2.

Referring to FIG. 2, the spinal fixation assembly 10 includes a plurality of spinal fixation devices 11 connected by a spinal fixation rod 12 that spans between the spinal fixation devices 11. Each spinal fixation device 11 can generally include a bone anchor 13, which can be a bone screw such as a pedicle screw, a bone anchor seat 17 and a locking cap 19. The bone anchor 13 is received within the bone anchor seat 17, such that the bone anchor seat 17 is coupled to the proximal end of the bone anchor 13, and the distal end of the bone anchor 13 is configured to be driven into the corresponding underlying vertebra 2. The bone anchor 13 can include a threaded shaft 60 that extends along a central axis 62, such that any suitable driver can apply a torsional force or torque to the bone anchor, thereby rotating the bone anchor 13 so as to cause the shaft 60 to be driven into the underlying vertebra 2. The bone anchor 13 can be inserted through the bone anchor seat 17 and subsequently driven into the underlying vertebra 2, or can be driven into the underlying vertebra 2 and the bone anchor seat 17 can be subsequently popped downward onto the head of the bone anchor 13. The bone anchor 13 can be rotated relative to the bone anchor seat 17 prior to locking the locking cap 19 in the bone anchor seat 17. The bone anchor seat 17 includes a first bearing surface 34 that is configured to receive the spinal fixation rod 12, and the locking cap 19 includes a second bearing surface 35 that is configured to secure the anchor seat 17 to the spinal fixation rod 12, such that the spinal fixation rod 12 is captured between the bearing surfaces 34 and 35 when the locking cap 19 is tightened to the bone anchor seat 17. Once the bone anchor 13 is implanted into the underlying vertebra 2 and attached to the bone anchor seat 17, the spinal fixation rod 12 can be received against the first bearing surface 34.

For instance, in accordance with the illustrated embodiment, the locking cap 19 defines external threads 61 that mate with internal threads of the bone anchor seat 17. The locking cap 19 further includes a recess 36 that is configured to receive a driving instrument that is configured to apply a torsional force or torque to the locking cap 19. Accordingly, the locking cap 19 can be actuated, such as rotated or screwed, between a first unlocked configuration and a second locked configuration whereby the spinal fixation rod 12 is captured between the bearing surfaces 34 and 35. When the locking cap 19 is in the unlocked configuration, the spinal fixation rod 12 can move with respect to the spinal fixation devices 11, and the bone anchors 13 can rotate relative to the respective bone anchor seat 17. When the locking cap 19 is in the locked configuration, such that the first bearing surface 34 and the second bearing surface 35 bear tightly against the spinal fixation rod 12, the spinal fixation rod 12 is unable to move with respect to the spinal fixation device 11. Furthermore, the locking cap 19 delivers a force to the bone anchor 13 that prevents the bone anchor 13 from rotating relative to the bone anchor seat 17. Unless otherwise specified, the spinal fixation assembly 10 and its components can be made from any suitable biocompatible material such as titanium, titanium alloys such as titanium-aluminum-niobium alloy (TAN), implant-grade 316L stainless steel, poly-ether-ether-ketone (PEEK) or any suitable alternative implant-grade material.

The spinal fixation devices 11 are each implanted into a corresponding plurality of underlying vertebra 2 disposed in a spinal region 1. While the spinal fixation rod 12 is illustrated as having a length sufficient to join four spinal fixation devices 11, it should be appreciated that the spinal fixation rod 12 can have any length suitable for attachment to any desired number of spinal fixation devices 11 configured to attach to any corresponding number of underlying vertebrae 2.

The spinal fixation rod 12 can extend substantially straight between a pair of opposing terminal ends 15a and 15b, and a middle portion 16 disposed between the terminal ends 15a and 15b, thereby defining a profile 14 that is substantially straight. While the profile 14 is substantially straight as illustrated, it should be appreciated that the spinal fixation rod 12 could be constructed as having a curved profile. For instance the middle portion 16 could be disposed posterior with respect to the terminal ends 15a and 15b when the spinal fixation devices 11 are implanted into the vertebrae 2, such that the spinal fixation rod 12 is concave with respect to the spinal column 3, though it should be appreciated that the spinal fixation rod 12 could also be curved when implanted such that the middle portion 16 is disposed anteriorly with respect to the terminal ends 15a and 15b, such that the spinal fixation rod 12 is convex with respect to the spinal column 3.

Referring to FIG. 3, the surgical assembly 41 can further include an implant manipulation instrument 20 configured to apply a compressive force against a pair of implanted spinal fixation devices 11, and subsequently lock the spinal fixation rod 12 in the spinal fixation devices 11. In accordance with the illustrated embodiment, the implant manipulation instrument 20 includes a torque assembly 21 and an actuator 22 connected such that the torque assembly 21 and the actuator 22 can move with respect to each other in multiple degrees of freedom. As illustrated, the torque assembly 21 and the actuator 22 can rotate, pivot and translate relative to each other while remaining operably connected.

The torque assembly 21 is configured as a driver 23 that includes a driver shaft 24 that extends along a central longitudinal axis L between a distal shaft portion 25, an opposed proximal shaft portion 26, and an intermediate shaft portion 27 that extends between the distal shaft portion 25 and the proximal shaft portion 26 along the longitudinal axis L. Thus, the distal shaft portion 25 and the proximal shaft portion 26 are spaced along the longitudinal axis L. The driver 23 also includes a handle 28 connected to the proximal shaft portion 26 of the driver shaft 24, the handle 28 being configured to receive a torque and transfer the received torque to the driver shaft 24. The actuator 22 includes a body 29 having a distal body portion 30, a proximal body portion 31 and an intermediate body portion 32 extending between the distal body portion 30 and the proximal body portion 31.

Referring to FIG. 4, the driver shaft 24 of the driver 23 extends along the longitudinal axis L, and defines an outer cross-sectional dimension D1, such as a diameter. In this regard, it should be appreciated that the driver shaft 24 can be substantially cylindrical or alternatively shaped as desired. The outer cross-sectional dimension D1 of the driver shaft 24 can vary at different locations along the driver shaft 24 from the proximal shaft portion 26 to the distal shaft portion 25. The implant manipulation instrument 20 includes a sleeve 33. The sleeve 33 is a tubular shape that is sized such that the outer cross-sectional dimension D1 of the driver shaft 24 fits within the sleeve 33. When the driver shaft 24 is positioned within the sleeve 33, the sleeve 33 can be coupled to the driver shaft 24 such that the sleeve 33 is able to rotate with respect to the driver shaft 24 about the longitudinal axis L. The implant manipulation instrument 20 can further include a connector 140 that couples the sleeve 33 to the driver shaft 24 as described above. The connector 140 prevents the sleeve 33 from falling off of the driver shaft 24, such as by translating along the longitudinal axis L, while allowing the driver shaft 24 to rotate with respect to the sleeve 33 about the longitudinal axis L. As illustrated, the connector 140 is a spring clip but it should be appreciated that other connectors or couplings could be used to operably couple the sleeve 33 and drive shaft 24 as described above.

Referring to FIGS. 2 and 4, the driver shaft 24 defines a distally directed tip 34 that defines a terminal end of the distal shaft portion 25. The tip 34 is configured to mate with the locking cap 19 in the recess 36, and can be tapered inwardly as it extends distally so as to facilitate insertion into the recess 36. The exact shape of the tip 34 and the recess 36 can be any of a number of shapes including but not limited to a flat head, a Phillips or crosshair end, a hex, or any other shape in which the tip 34 and recess 36 have some corresponding features that allow the tip 34 to enter the recess 36 and impart a torque on the locking cap 19 to rotate the locking cap 19 from the unlocked configuration to the locked configuration and vice versa.

The handle 28 can extend proximally from the driver shaft 24, and can be integral with the driver shaft 24 or can alternatively be discreetly attached to the driver shaft 24 via coupling 37. The coupling 37 is configured to rotationally lock the handle 28 with respect to the driver shaft 24, such that a torsional force or torque applied to the handle 28 is transferred to through the coupling 37 to the driver shaft 24. Thus, the coupling 37 can include corresponding engagement members, such as an internal hex and an external hex that mate, on the driver shaft 24 and handle 28 that rotatably couple the handle 28 to the driver shaft 24. One example of corresponding engagement drives would be an internal hex and an external hex. Handle 28 may also include a built in torque limiter 38 that prevents over tightening of the locking cap 19 when being fixed to the anchor seat 17. Accordingly, the handle 28 is rotatably coupled to the proximal shaft portion 25, such that a rotational biasing force applied to the handle 28 is transferred to the distal shaft portion 25 and the tip 34.

The handle 28 can be configured as desired, and includes a substantially T-shaped grip 39 presenting an engagement surface 40. The grip 39 can be sized to allow a surgeon's hand to grab and apply a torque to the handle 28. It should be appreciated that the grip 39 can be any structure or handle suitable for a surgeon to grab and apply a torque to such as but not limited to a knob, crank, protrusion, and the like. The driver 23 is configured to receive a torque, and selectively transfer the torque to the locking caps 19, so as to move the locking caps to the locked configuration.

Referring now to FIGS. 5A and 5B, the actuator 22 includes an actuator body 29 that has a proximal body portion 31, an opposed distal body portion 30, and an intermediate body portion 32 that extends between the proximal body portion 31 and the distal body portion 30. The body 29 is defined by a top surface 42, a bottom surface 43, and opposing side surfaces 44. Alternatively, the body 29 can have a circular cross-section or can define any suitable alternative shape as desired.

The proximal body portion 31 includes a substantially flat panel 45 that is configured to receive a force F and impart that received force F to the distal body portion 30. The top surface 42 and the bottom surface 43 can be wider at the panel 45 than at the intermediate body portion 32, such that the actuator body 29 necks down from the panel 45 to the intermediate body portion 32. The broader top surface 42 and broader bottom surface 43 allow for easier input of a force to the actuator 22 than at the intermediate body portion 32. The intermediate body portion 32 defines a recess 46 that extends from the top surface 42 through the bottom surface 43. The recess 46 has a length L1 defined by a top inner wall 47 and a bottom inner wall 48 and a width W defined by opposing side walls 49. The width is substantially equal to or slightly greater than the outer cross-sectional dimension D2 of the driver shaft 24 such that the driver shaft is configured to extend through the recess 46 between the side walls 49. The distal body portion 30 includes a body tip 50 and a neck 53 that connects the body tip 50 to the intermediate body portion 32. The neck 53 can extend obliquely with respect to the intermediate body portion 32, such that the body tip 50 is offset from the rest of the intermediate body portion 32. The body tip 50 includes a distal end 51 that is configured to slidably and releasably contact the spinal fixation rod 12 (shown in FIG. 2). The distal end 51 can define a curved surface 52 having a curvature that matches the radius of the spinal fixation rod 12 (see FIG. 2).

During operation, with further reference to FIG. 6, a first spinal fixation device 11 is attached to a first vertebra 2 and a second spinal fixation device 11' is attached to a second vertebra 2' in the manner described above. In particular, each of the bone anchors 13 and 13' of the spinal fixation devices 11 and 11' are received by the anchor seats 17 and 17', respectively. Furthermore, the bone anchors 13 and 13' are attached to the vertebrae 2 and 2' respectively, for instance, by screwing the bone anchors 13 and 13' into the pedicles of the vertebrae 2 and 2'. The spinal fixation rod 12 is inserted through each of the anchor seats 17 and 17' and placed in a desired position with respect to at least the second spinal fixation device 11'. The locking cap 19' of the second spinal fixation device 11' is moved into the locked configuration such that spinal fixation rod 12 and the second spinal fixation device 11' cannot move with respect to each other. For instance, the tip 34 of the driver 23 is inserted into the recess 36 of the locking cap 19' (see FIG. 2), and the driver 23 is rotated so as to tighten the locking cap 19' against the spinal fixation rod 12. The locking cap 19 of the first spinal fixation member 11 remains in the unlocked configuration such that the spinal fixation rod 12 and the first spinal fixation member 11 can move with respect to each other.

The implant manipulation instrument 20 can further secure the spinal fixation assembly 10. For instance, the driver 23 is positioned such that the intermediate shaft portion 27 is disposed within the recess 46 of the body 29 of the actuator 22. Thus, the driver 23 and the actuator 22 intersect. The outer cross-sectional dimension D1 of the intermediate shaft portion 27 and the width W of the recess 46 are sized such that the driver 23 and the actuator 22 can freely translate longitudinally with respect to each other, rotate about their respective central longitudinal axes with respect to each other, and pivot with respect to each other about respective axes angularly offset, e.g., perpendicular, with respect to their central longitudinal axes.

The tip 34 of the driver 23 is moved into the recess 36 of the locking cap 19. The body tip 50 of the distal body portion 30 is moved into contact with the spinal fixation rod 12 and the second spinal fixation device 11'. Specifically, the curved surface 52 of the distal end 51 is manipulated into slidable and releasable contact with the spinal fixation rod 12 and the bottom surface 43 at the body tip 50 of the actuator 22 is manipulated into releasable contact with the anchor seat 17'.

Once both the tip 34 of the driver 23 and the body tip 50 of the actuator 22 are in contact with the spinal fixation assembly 10 as described above, a force F is applied to the bottom surface 43' of the panel 45 and to the sleeve 33. The force F biases the proximal body portion 31 toward the driver 23, thereby causing the actuator 22 to pivot with respect to the driver 23 about a location where the top inner wall 47 contacts the intermediate shaft portion 27. As the proximal body portion 31 pivots toward the proximal shaft portion 26 the distal body portion 30 pivots toward the distal shaft portion 25. As a result the second spinal fixation device 11' moves closer to the first spinal fixation device 11, thereby compressing the vertebrae 2 and 2'. Once the desired level of compression is achieved, a torque is applied to the grip 39, and thus the handle 28. The applied torque is transferred to the tip 34 that imparts the torque to the locking cap 19, thereby rotating the locking cap 19 from the unlocked configuration to the locked configuration. The torque can be continuously applied until a specified torque is achieved placing the locking cap 19 in the locked configuration. Because the driver shaft 24 is able to rotate with respect to the sleeve 33 as described above in reference to FIG. 4, force F can be applied continuously to the actuator 22 and the sleeve 33 while the locking cap 19 is rotated to the locked configuration. For instance, a single surgeon can apply force F to the actuator 22 and the sleeve 33 with one hand while applying the torque to the grip 39 with the other hand. The rotational coupling of the sleeve 33 and the driver shaft 24 allows the surgeon's hand to remain in place on the sleeve 33 applying the force F while the driver shaft 24 rotates within the sleeve 33 transferring the torque from the grip 39 to the tip 34. It should be appreciated that the steps described above for fixing the spinal fixation assembly 10 as described above may be rearranged as desired.

Referring to FIGS. 7A and 8, the surgical assembly 41 can further include an anchor delivery instrument 300 that is configured to guide a bone anchor to a target location, such as an underlying vertebra, in a desired position and orientation.

In accordance with the illustrated embodiment, the anchor delivery instrument 300 includes a handle 301 and a guide 302 connected to the handle 301. The handle 301 includes a body 303 that is elongate along a central longitudinal axis 306, and defines a proximal end 304 and a distal end 305 that is spaced from the proximal end 304 along the longitudinal axis 306. The guide 302 is elongate along a central axis 310 that can be angularly offset with respect to the longitudinal axis 306, and includes a cannulated body 307 having a first portion 308 that can define a head 318, and a second portion 309 spaced from the first portion 308 along the central axis 310. The second portion 309 can define a shaft 320 that extends distally from the head 318.

The handle 301 includes a grip 315, such that the body 303 supports the grip 315 and connects the grip to the guide 302. The body 303 includes a first or proximal arm 322 that extends distally from the grip 315 inline with the longitudinal axis 306, and a second or distal arm 324 that extends distally from the first or proximal arm 322, and defines the distal end 305 of the handle 301. The body 303 further includes a transition arm 314 connected between the first or proximal arm 322 and the second or distal arm 324. The transition arm 314 can extend along a direction that is angularly offset with respect to the longitudinal axis 306, such that the second or distal arm 324 is offset with respect to the first or proximal arm 322 along a direction angularly offset with respect to the longitudinal axis 306. For instance, the second or distal arm 324 can be spaced closer to the distal end # of the guide 302. The distal arm 324 can be attached to the head 318 of the cannulated body 307 as illustrated, or can be connected to the guide 302 at any alternative location along the cannulated body 307, such as the shaft 320.

The guide 302, including the cannulated body 307, can be made from a radiolucent material, meaning that it can be seen through in an x-ray, unless otherwise indicated. The cannulated body 307 defines a first or proximal end 308 and a second or distal end 309 that is spaced from the first or proximal end 308 along the central axis 310. In accordance with the illustrated embodiment, the handle 301 is attached to the cannulated body 307 at the proximal end 308, though it should be appreciated that the handle 301 can be attached to the guide 302 at any alternatively location as desired. The head 318 of the cannulated body 307 can define a cross-sectional dimension greater than that of the shaft 320, though it should be appreciated that the head 318 can define a cross-sectional dimension less than that of the shaft 320, or substantially equal to that of the shaft 320. It should be appreciated that the cannulated body 307 can be devoid of the head 318, such that the shaft 320 of the cannulated body 307 extends from the proximal end 308 of the cannulated body 307 to the distal end 309.

The guide 302 defines a cannulation 311 that extends along the central axis 310 through the cannulated body 307, and can extend through both the first and second ends 308 and 309. The second end 309 includes a tip 312 that defines at least one tooth such as a plurality of teeth 317. The tip 312 can be round or substantially circular, or can define any suitable alternative shape as desired. In accordance with the illustrated embodiment, the tip 312 defines a tapered profile along the circumferential direction, so as to define a distal point 331. The tip 312 can be made from a radio-opaque material, which is more radio-opaque than the radiolucent material. The teeth 317 are configured to be driven into an underlying bone, such as a vertebra so as to secure the anchor delivery instrument 300 to the underlying bone. Thus, during a surgical delivery of a spinal fixation device 11, a surgical component can be guided through the cannulation 311 to the underlying bone. The surgical component can be, for instance, a bone anchor 13 that is subsequently implanted in the underlying bone, a drill bit that is configured to produce a recess in the underlying bone, such that the recess is configured to receive the bone anchor 13, a guide wire or Kirschner wire that facilitates implantation of the bone anchor 13 in the underlying bone, a fiduciary marker 7 (see FIGS. 10-11J), or any other surgical component as desired. Thus, the cannulation 311 can define a cross-sectional dimension sized substantially equal to or slightly greater than the surgical component that is guided through the cannulation 311.

With continuing reference to FIGS. 7A and 8, the guide 302 can include a first set 326 of at least one first radio-opaque marker 313, such as a plurality of first radio-opaque markers 313a-313d, and a second set 328 of at least one second radio-opaque marker 330 such as a plurality of second radio-opaque markers 330. For instance, as descried above, the tip 312 can be radio-opaque so as to define the second radio-opaque marker 330. The first set 326 of radio-opaque markers 313 can be carried by the guide 302 at any location spaced from the second radio-opaque marker 330 as desired. For instance, the first set 326 of radio-opaque markers 313 can be at least partially embedded in the cannulated body 307. In accordance with the illustrated embodiment, the head 318 includes a radially outer portion 332 and an inner portion 334 that is distally recessed with respect to the outer portion 332, such that the outer portion 332 defines a radially inner surface 336 that defines a radially outer perimeter of a void 338 that is disposed proximal of the proximally outer surface of the inner portion 334. The cannulation 311 extends through the inner portion 334 in accordance with the illustrated embodiment. The first plurality of radio-opaque markers 313a-d can be driven at least partially into the radially inner surface 336, and thus at least partially embedded in the head 318. In accordance with the illustrated embodiment, the first plurality of radio-opaque markers 313 are partially embedded in the head 318, though it should be appreciated that the first plurality of radio-opaque markers 313 can alternatively be fully embedded in the head 318. Alternatively still, the first plurality of radio-opaque markers 313 can be carried by the guide at any location proximal of the second radio-opaque marker 330 as desired. For instance, the first plurality of radio-opaque markers 313 can be at least partially embedded in or otherwise carried by the cannulated body 307 at any location proximal of the tip 312.

In accordance with the illustrated embodiment, the first set 326 of at least one radio-opaque markers 313 includes a plurality of radio-opaque markers 313 that are substantially equidistantly spaced circumferentially with respect to each other. While four radio-opaque markers 313 a-d are illustrated as spaced substantially 90° with respect to each other, the first set 326 of markers 313 can include any number of radio opaque markers 313 greater than or equal to one. It should be further appreciated that the plurality of radio-opaque markers 313 can alternatively be variably spaced from each other as desired. Furthermore, in accordance with the illustrated embodiment, the radio-opaque markers 313 define a first opposed pair 313a and 313c, and a second opposed pair 313b and 313d. The first set 326 of markers 313 further defines a first axis 340 that extends centrally through the first opposed pair 313a and 313c of radio-opaque markers, and a second axis 342 that extends centrally through the second opposed pair 313b and 313d of radio-opaque markers. In accordance with the illustrated embodiment, the axes 340 and 342 define an intersection 344.

Referring also to FIGS. 9A-B, the radio-opaque markers 313 and the circular tip 312 are shown in solid lines to represent their visibility in a radio image while the remainder of the guide 302 is shown in dotted lines to identify radiolucent material in the radio image. In accordance with the illustrated embodiment, the first and second sets 326 and 328 of at least one radio-opaque marker can be spatially positioned as desired to indicate that the guide 302, and in particular the cannulated body 307, is in a desired orientation with respect to a target location of an underlying bone. For instance, when distal point 331 of the tip 312 is driven into the underlying bone, such as a pedicle or a vertebra, and the cannulated body 307 is oriented as desired, the surgical component, such as the bone anchor 13 can be driven into the pedicle so as to remain contained in the pedicle as it is driven into the vertebra. It is appreciated that an improperly oriented bone anchor 13 or other surgical component can pierce the outer periphery of the pedicle or otherwise damage the pedicle or vertebra when driven into the vertebra. If the cannulated body 307 is found to be in an undesired orientation after the point 331 has been driven into the underlying target location, the orientation of the cannulated body 307 can be corrected to the desired orientation prior to driving the remainder of the tip 312 into the underlying bone and subsequently implanting the surgical component in the underlying bone.

The actual orientation of the cannulated body 307 can be determined as desired or undesired based on a spatial relationship between the first and second sets 326 and 328 of radio-opaque markers. For instance, when the cannulated body 307 is oriented as desired, the radio image of the tip 312 is disposed at a desired location with respect to at least one of the first set 326 of radio-opaque markers 313. When the cannulated body 307 is undesirably oriented, the radio image of the tip 312 is disposed at a location other than the desired location with respect to at least one of the first set 326 of radio-opaque markers 313. For instance, in accordance with the illustrated embodiment, the desired location of the tip 312 relative to the at least one radio-opaque marker 313 of the first set 326 of radio-opaque markers 313 is substantially centered with respect to the radio-opaque markers 313a-d. In accordance with the illustrated embodiment, the intersection 344 of the axes 340 and 342 of the radio-opaque markers 313a-d is disposed substantially at the centroid 346 of the tip 312, as illustrated in FIG. 9A. When the cannulated body 307 is undesirably oriented, the radio image of the tip 312 is positioned such that the centroid 346 of the tip 312 is offset with respect to intersection 344 of the axes 340 and 342. It should be appreciated that the actual orientation of the cannulated body 307 can be compared to the desired orientation to determine if the actual orientation is in the desired orientation or an undesirable orientation from a view substantially inline with the central axis, or other known desired orientation, with respect to the underlying target location, which can be the pedicle of the underlying vertebra. Thus, the view can be an anterior-posterior view of a fluoroscopic image, or the view can be laterally oblique with respect to an anterior-posterior view.

Figure 7B:
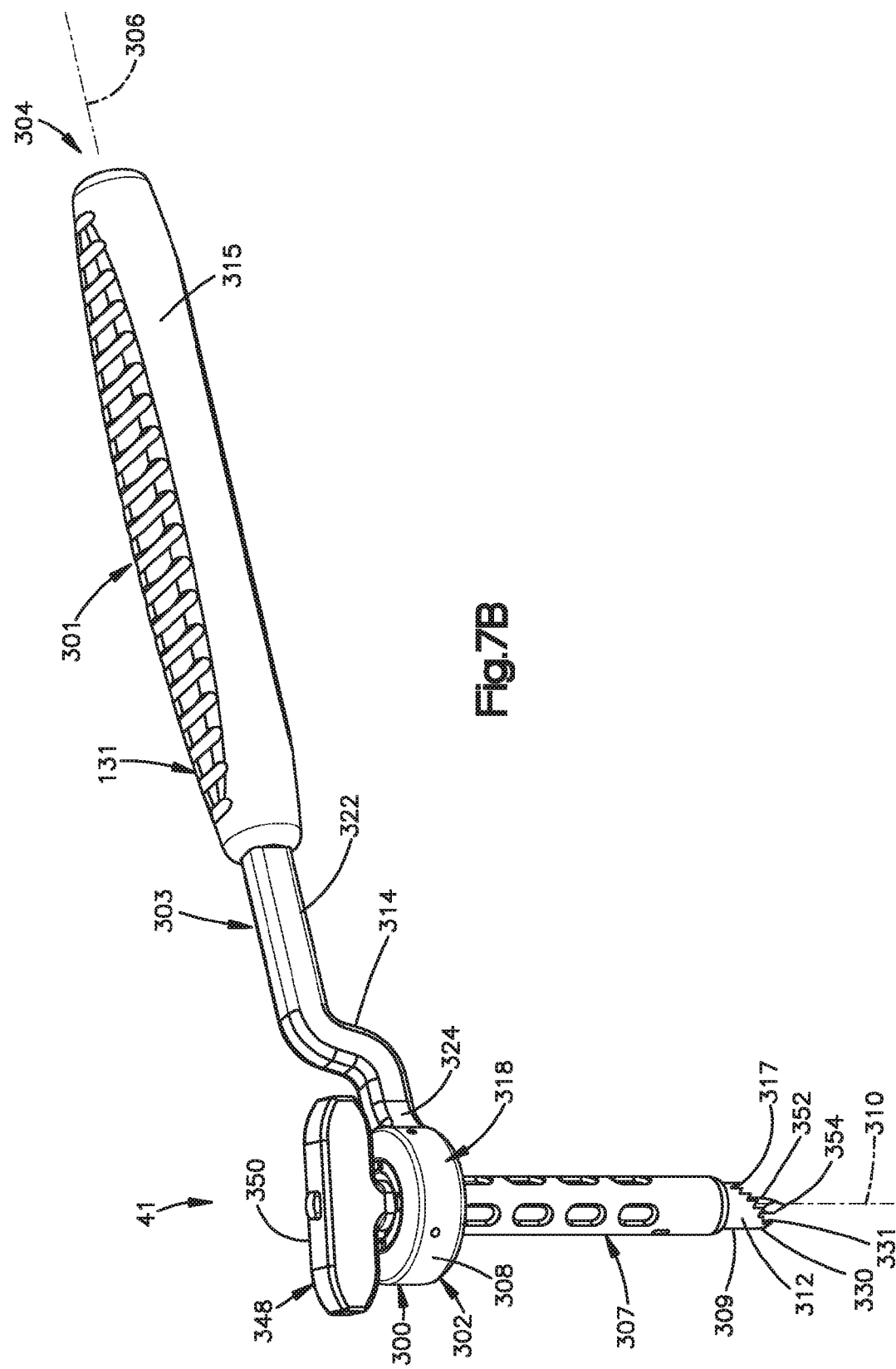
FIG. 7B is a perspective view of an anchor delivery assembly including the anchor delivery instrument illustrated in FIG. 7A and a trocar inserted into the guide of the anchor delivery instrument.

Referring now to FIG. 7B, the surgical assembly 41 can further include an anchor delivery assembly 131 that includes the anchor delivery instrument 300 and a trocar 348 that is configured to be inserted through the cannulation 311 of the guide 302, and driven into the cortical wall of the underlying bone, e.g., pedicle, once the actual orientation of the cannulated body 307 has achieved the desired orientation. The trocar 348 can include a head 350 and a shaft 352 that extends distally from the head 350, and a tip 354 that extends distally from the shaft 352. The shaft 352 has a cross-sectional dimension substantially equal to or slightly less than that of the cannulation 311, such that the cannulated body 307 can guide the shaft 352 distally as the shaft 352 translates in the cannulation 311. The head 350 defines a cross sectional dimension greater than that of the shaft, such that the head 350 abuts the proximal end of the guide 302 when the trocar 348 has been fully translated distally within the cannulation 311. Once the trocar 348 has been fully translated distally, the tip 354 protrudes distally beyond the point 331 of the tip 312 of the shaft 320, such that the tip 354 of the trocar 348 can pierce the cortical wall of the underlying bone at an insertion point without causing the tip 312 of the cannulated body 307 to also pierce the cortical wall of the underlying bone. The tip 354 can be driven through the cortical wall and into the cancellous portion of the target bone.

Accordingly, during operation, a radio image of the guide 302 and spinal region is examined to determine whether the guide 302 is in the desired orientation or an undesired orientation. If the guide 302 is in an undesired orientation, the cannulated body 307 can be pivoted until it is determined that the cannulated body 307 is in the desired orientation. Once the actual orientation of the cannulated body 307 is the same as the desired orientation, the trocar 348 can be tapped, for instance at the head 350, using a mallet or any suitable alternative device so as to drive the trocar tip 354 through the cortical wall of the underlying target bone so as to create a pilot hole in the underlying bone. It should be further appreciated that the teeth 317 can be caused to grip the underlying bone before or while the guide 302 is oriented as desired. For instance, a mallet or any suitable alternative device can tap the proximal end 308, or head 318, of the cannulated body 307 so as to cause the teeth 314 to bite into the cortical wall of the underlying bone prior to driving the trocar through the cortical wall.

Next, the trocar 348 can be translated proximally so as to remove the tip 354 from the underlying bone and further remove the trocar 348 from the cannulation 311, and a surgical component can next be inserted into the cannulation 311 and driven distally into the pilot hole created by the trocar 348. For instance, the bone anchor 13, without the bone anchor seat 17 attached, can be inserted into the cannulation 311, which can be sized substantially equal to or slightly greater than the head of the bone anchor 13. The driver instrument of the bone anchor 13 can translate the bone anchor 13 distally through the cannulation 311, and rotate the bone anchor 13 such that the tip of the threaded bone anchor shaft 60 is driven into the underlying bone through the pilot hole created by the trocar 348. Once the bone anchor 13 has been driven into the underlying bone, the guide 302 can be removed from the bone anchor 13 by translating the cannulated body 307 proximally until the cannulation 311 has cleared the bone anchor head. Once the guide 302 has been removed, the bone anchor seat 17 can be popped downward onto the head of the bone anchor 13 as described above.

Figure 10:
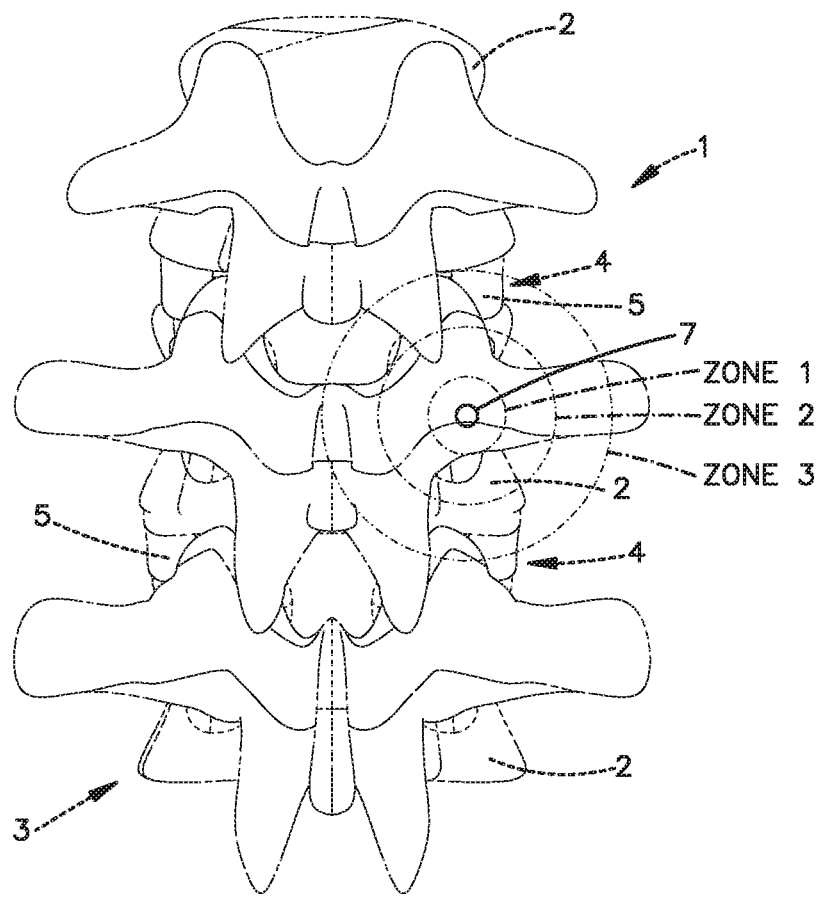
FIG. 10 is a rear elevation view of adjacent vertebrae and intervertebral spaces showing the placement of a pedicle fiducial marker as an intra-operative reference point and a stable mount for various surgical instruments.

As described above, the surgical component can define a fiduciary marker 7, which can include the bone anchor 13, or any alternative structure that can be implanted in the underlying bone (see FIGS. 10-11J). Thus, the fiduciary marker 7 can be driven through the cannulation 311 and into the pilot hole created by the trocar 348 as described above with respect to the bone anchor 13. Alternatively or additionally, once the trocar 348 has been driven through the cortical wall of the underlying bone and subsequently removed, a drill bit can be driven distally through the cannulation 311 and into the pilot hole created by the trocar 348, and subsequently further into the underlying bone. The drill bit can subsequently be removed, and the bone anchor 13 or other fiduciary marker 7 can be subsequently inserted in the pilot hole created by the drill bit.

Referring now to FIG. 10, the fiduciary marker can be configured as the bone anchor 13 as described above, or any alternative radiographically visible pedicle reference implant. For instance, the fiducial marker 7 is inserted into a patient's vertebra 2, such as the pedicle, and provides a distinct reference marker to aid the surgeon in fluoroscopically navigating the surgical workspace. The fiducial marker 7 provides a reference point from which the surgeon can generally identify several noteworthy areas of the spinal region 1 including the lamina 6, disc space 4, exiting nerve roots, and other anatomical structures of a vertebra 2 prior to, and during, decompressive surgical procedures. For instance, Zone 1 identifies the boney region immediately adjacent to the fiducial marker 7. This area provides a desired navigational reference location, such as the pedicle. Zone 2, as illustrated, can be bounded by the disc space 4 at the cranial aspect (typical surgical target) and the exiting nerve root in the lateral, caudal quadrant. Zone 3, as illustrated, can extend to the cranialmost side of both the cranial disc space 4 adjacent to the boney region identified by Zone 1 and the caudal disc space 4 adjacent to the boney region identified by Zone 1. By marking a known pedicle position, the surgeon can maintain a navigable reference even after the patient's anatomy has been significantly altered during the surgical procedure.

Referring now to FIGS. 11A-11J, the fiducial markers 7 can provide non-ambiguous anchoring locations or mounting posts for attachment of various surgical instruments, such as access ports, retractor blades, suction tubes, targeting devices, drill guides or endoscopic instruments, that may be used when performing decompression, fusion, and fixation procedures of the spine. The various fiducial markers 7 can be constructed as desired, for instance as illustrated by the fiducial markers 7a-7f illustrated in FIGS. 11A-11J, or alternatively as illustrated by the bone anchor 13.

Referring to FIG. 11A, the fiducial marker 7a is illustrated as a spinal fixation device 11, including the bone anchor 13 and the bone anchor seat 17 as described above. Referring to FIG. 11B, the fiducial marker 7b is illustrated as the bone anchor 13 of FIG. 11A, including a shaft 8 presenting external threads 9, and a head 137 having a substantially spherical outer surface 139. As described above, the bone anchor seat 17 can be popped onto the outer surface 139 of the head 137 after the shaft 8 has been driven into the underlying bone. As illustrated in FIGS. 11C-G, the fiducial markers 7c-7e can include a shaft 8 and a head 137 disposed at the proximal end of the shaft 8. The heads 137 can be constructed in accordance with any embodiment as desired. Various heads are illustrated in FIGS. 11C-G. It should be appreciated, however, that the fiducial markers 7 can be provided without heads, and that the shafts 8 can be constructed in accordance with any embodiment as desired. For instance, as illustrated in FIG. 11I, the shaft 8 can be unthreaded. Each of the fiducial markers 7a-7f can define a cannulation extending longitudinally through the shaft 8 that is configured, for instance, to receive a guide wire that extends into the underlying bone. The markers 7a-7f may be further designed to accommodate any number of degrees of freedom of movement of the attached instrumentation. The mechanisms to orient and/or secure the instruments in the surgical site may be a function of the markers 7a-7f, the surgical instrument, or both. The markers 7a-7f can be removed prior to closing the surgical site or, alternately, the markers 7a-7f can be retained as one of the elements of the fixation hardware to be used in the surgical procedure, such as the embodiment shown for marker 7a, in which a spinal fixation device 11, including a bone anchor 13 and an anchor seat 17, is used as the marker device, or the embodiment shown for marker 7b, in which a bone anchor 13 is used as the marker device and a bottom-loading or "pop-on" anchor seat 17 is coupled over the head 137 of the bone anchor 13. Pedicle targeting aids, such as the anchor delivery instrument 300 described above can also be coupled to the various fiducial markers 7a-7f. The void created in the underlying bone during insertion of the fiducial markers 7a-7f may subsequently define a pilot hole for placing permanent hardware, such as spinal fixation devices 11, after removal of the fiducial marker 7. The markers 7a-7f may be formed of radio-opaque material or include radio-opaque portions or elements for fluoroscopic visibility. In some embodiments, the fiducial markers 7a-7f and/or other components of the related system can be disposable.

Although the disclosure has been described in detail, it should be understood that various changes, substitutions, and alterations can be made herein without departing from the spirit and scope of the invention as defined by the appended claims. For instance, it should be appreciated that the cross-sectional dimensions described herein can define diameters, unless otherwise indicated. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A surgical instrument for securing a spinal fixation rod with a first and a second spinal fixation device, the surgical instrument comprising:
   a driver configured to apply torque to a locking cap of the first spinal fixation device, so as to lock the locking cap against the spinal fixation rod, the driver defining a longitudinal axis, a proximal end, and a distal end opposite the proximal end along the longitudinal axis, such that the driver is elongate along the longitudinal axis, the driver also comprising a driver shaft located between the proximal end and the distal end;
   the driver shaft located within and extending through a tubular sleeve such that: (i) the shaft of the driver is rotatable with respect to the sleeve about the longitudinal axis and (ii) the sleeve is prevented from translating along the longitudinal axis of the driver; and
   an actuator comprising (1) a distal end that is configured to fit over the spinal fixation rod, (2) a proximal end opposite the distal end, (3) a proximal body portion located distally of the proximal end, (4) a distal body portion located proximally of the distal end, and (5) an intermediate body portion located between the proximal body portion and the distal body portion, wherein the intermediate body portion defines a recess sized to receive the shaft of the driver such that the shaft of the driver extends through the recess;
   wherein the distal end, proximal end, proximal body portion, distal body portion, and intermediate body portion of the actuator are integrally formed together, and
   wherein the actuator pivots, translates, and rotates about shaft of the driver.

2. The surgical instrument of claim 1, wherein a force applied to the proximal portion of the actuator causes the actuator to pivot with respect to the driver such that the proximal end of the actuator moves closer to the proximal end of the driver and the distal end of the actuator moves closer to the distal end of the driver.

3. The surgical instrument of claim 2, further comprising a tip connected to the distal end of the shaft of the driver, the tip configured to define an interference fit with the first spinal fixation device.

4. The surgical instrument of claim 3, wherein the distal end of the actuator is configured to be coupled to the second spinal fixation device.

5. The surgical instrument of claim 4, wherein the distal end of the actuator comprises a tip that is configured to be coupled to the second spinal fixation device.

6. The surgical instrument of claim 5, wherein the tip of the actuator comprises a surface which is configured to contact and impart a force to the second spinal fixation device.

7. The surgical instrument of claim 6, wherein the tip of the actuator comprises a bottom surface that has a radius configured to slidably and releasably translate along the spinal fixation rod.

8. The surgical instrument of claim 1, wherein the entirety of the sleeve is located adjacent to the shaft of the driver at a position proximally to the recess of the actuator.

9. The surgical instrument of claim 8, wherein the actuator can pivot, translate, and rotate about the shaft of the driver simultaneously.

10. A surgical instrument for securing a spinal fixation rod with a first and a second spinal fixation device, the surgical instrument comprising:
    a driver including a longitudinal axis, the driver being elongate along the longitudinal axis in a first direction, the driver defining a proximal end, a distal end opposite the proximal end along the longitudinal axis, and a shaft located between the proximal end and the distal end, the shaft having a first elongated side surface and an opposite second elongated side surface where the first and second side surfaces extend along the shaft in the first direction, the distal end of the driver configured to apply a torque to a locking cap of the first spinal fixation device, so as to lock the locking cap against the spinal fixation rod;
    the shaft of the driver extending within and through a tubular sleeve such that: (i) the shaft of the driver is rotatable with respect to the sleeve about the longitudinal axis and (ii) the sleeve is prevented from translating along the shaft of the driver in the first direction; and
    an actuator comprising (1) a proximal portion with a proximal end; (2) a distal portion with a distal end; and (3) an intermediate portion located between the proximal portion and the distal portion where the intermediate portion comprises an enclosed recess;
    wherein the shaft of the driver is positioned within and through the enclosed recess of the actuator such that the entirety of the proximal portion of the actuator is positioned adjacent to the first side surface of the shaft of the driver and the entirety of the distal portion of the actuator is positioned adjacent to the second side surface of the shaft of the driver, and the entirety of the sleeve is positioned proximally of the recess of the actuator; and
    wherein the actuator pivots, translates, and rotates about the shaft of the driver.

11. The surgical instrument of claim 10, further comprising a tip connected to the distal end of the shaft of the driver, the tip configured to define an interference fit with the first spinal fixation device.

12. The surgical instrument of claim 11, wherein the distal end of the actuator is configured to be coupled to the second spinal fixation device.

13. The surgical instrument of claim 12, wherein the distal end of the actuator comprises a tip that is configured to be coupled to the second spinal fixation device.

14. The surgical instrument of claim 13, wherein the tip of the actuator comprises a surface which is configured to contact and impart a force to the second spinal fixation device.

15. The surgical instrument of claim 14, wherein the tip of the actuator comprises a bottom surface that has a radius configured to slidably and releasably translate along the spinal fixation rod.

16. The surgical instrument of claim 10, wherein a force applied to the proximal portion of the actuator causes the actuator to pivot with respect to the shaft of the driver such that the proximal end of the actuator moves closer to the proximal end of the driver and the distal end of the actuator moves closer to the distal end of the driver.

17. The surgical instrument of claim 16, wherein the actuator can pivot, translate, and rotate about the shaft of the driver simultaneously.

* * * * *